US010557047B2

(12) United States Patent
Reichert et al.

(10) Patent No.: US 10,557,047 B2
(45) Date of Patent: Feb. 11, 2020

(54) GA-NAPHTHALOCYANINE CHROMOPHORES WITH SHORT CHAIN ALKOXY AXIAL SUBSTITUENTS

(71) Applicant: BASF SE, Ludwigshafen (DE)

(72) Inventors: Hans Reichert, Rheinfelden (DE); Yves Bron, Delemont (CH); Helmut Reichelt, Neustadt (DE); Marina Schiller, Rheinfelden (DE)

(73) Assignee: BASF SE, Ludwigshafen (DE)

( * ) Notice: Subject to any disclaimer, the term of this patent is extended or adjusted under 35 U.S.C. 154(b) by 33 days.

(21) Appl. No.: 15/307,964

(22) PCT Filed: Apr. 30, 2015

(86) PCT No.: PCT/EP2015/059588
§ 371 (c)(1),
(2) Date: Oct. 31, 2016

(87) PCT Pub. No.: WO2015/169701
PCT Pub. Date: Nov. 12, 2015

(65) Prior Publication Data
US 2017/0051166 A1    Feb. 23, 2017

(30) Foreign Application Priority Data

May 5, 2014    (EP) .................................... 14166992

(51) Int. Cl.
C09D 11/037    (2014.01)
C09B 47/04    (2006.01)
C07D 487/22    (2006.01)
C09D 11/322    (2014.01)

(52) U.S. Cl.
CPC .......... C09D 11/037 (2013.01); C07D 487/22 (2013.01); C09B 47/04 (2013.01); C09B 47/045 (2013.01); C09D 11/322 (2013.01)

(58) Field of Classification Search
CPC ...... C09D 11/037; C07D 487/22; C09B 47/04
See application file for complete search history.

(56) References Cited

U.S. PATENT DOCUMENTS

| 7,122,076 | B2* | 10/2006 | Vonwiller | C09B 47/00 106/31.13 |
|---|---|---|---|---|
| 7,671,194 | B2 | 3/2010 | Indusegaram et al. | |
| 2006/0030704 | A1 | 2/2006 | Vonwiller et al. | |
| 2006/0030706 | A1 | 2/2006 | Vonwiller et al. | |
| 2006/0272545 | A1 | 12/2006 | Vonwiller et al. | |
| 2007/0008392 | A1 | 1/2007 | Vonwiller et al. | |
| 2008/0087192 | A1 | 4/2008 | Starling et al. | |
| 2008/0241492 | A1 | 10/2008 | Demartin Maeder et al. | |
| 2009/0035533 | A1 | 2/2009 | Starling et al. | |
| 2009/0043108 | A1* | 2/2009 | Indusegaram | C07D 209/56 548/427 |
| 2009/0242642 | A1 | 10/2009 | Starling et al. | |
| 2009/0255986 | A1 | 10/2009 | Starling et al. | |
| 2009/0266877 | A1 | 10/2009 | Vonwiller et al. | |
| 2011/0027550 | A1 | 2/2011 | Vonwiller et al. | |
| 2011/0048259 | A1 | 3/2011 | Starling et al. | |
| 2011/0069127 | A1 | 3/2011 | Indusegaram et al. | |

FOREIGN PATENT DOCUMENTS

| JP | 2005-507453 A | 3/2005 |
|---|---|---|
| WO | WO 03/038003 A1 | 5/2003 |
| WO | 2006/015414 A1 | 2/2006 |
| WO | 2007/002982 A1 | 1/2007 |
| WO | 2008/046129 A1 | 4/2008 |
| WO | 2008/006135 A1 | 7/2008 |
| WO | 2009/012514 A1 | 1/2009 |
| WO | 2009/015407 A1 | 2/2009 |

OTHER PUBLICATIONS

International Search Report dated Jul. 15, 2015 in PCT/EP2015/059588 filed Apr. 30, 2015.

* cited by examiner

Primary Examiner — Robert D Harlan
(74) Attorney, Agent, or Firm — Oblon, McClelland, Maier & Neustadt, L.L.P.

(57) ABSTRACT

The present invention relates to specific Ga-naphthalocyanine chromophores with short chain alkoxy axial substituents, their use as almost colourless IR absorbers, for optical filter applications; especially for plasma display panels, or for laser welding of plastics. The compounds may be used in compositions for inks, paints and plastics, especially in a wide variety of printing systems and are particularly well-suited for security applications.

19 Claims, No Drawings

GA-NAPHTHALOCYANINE CHROMOPHORES WITH SHORT CHAIN ALKOXY AXIAL SUBSTITUENTS

The present invention relates to specific Ga-naphthalocyanine chromophores with short chain alkoxy axial substituents, their use as almost colourless IR absorbers, for optical filter applications, especially for plasma display panels, or for laser welding of plastics. The compounds may be used in compositions for inks, paints and plastics, especially in a wide variety of printing systems and are particularly well-suited for security applications.

DESCRIPTION OF THE RELATED ART

Colourless, or at least barely coloured, IR absorbers meet a significant technical need in a wide range of applications, such as security printing (bank notes, credit cards, identity cards, passports etc.), invisible and/or IR readable bar codes, the laser-welding of plastics, the curing of surface-coatings using IR radiators, the drying and curing of print, the fixing of toners on paper or plastics, optical filters for PDPs (plasma display panels), laser marking e.g. of paper or plastics, the heating of plastic preforms, heat shielding applications, etc.

A large number of organic and inorganic substances belonging to different compound classes and with a great variety of different structures are known for the application as IR absorbers. Notwithstanding that large numbers of known compound classes and structures with a complex profile of properties often presents difficulties, there is a continuing demand for IR absorbers that are "colourless" (i.e. with the minimum possible inherent colour), and that simultaneously meet the technical stability requirements (chemical stability, heat stability and/or light stability).

A special field of application for colourless IR absorbers regards inks for printing processes which are used for printing currency and other security documents, also referred to as "security printing". Typical security printing processes are processes, wherein an ink composition is employed that is designed to selectively absorb radiation in parts of the "optical infrared" spectrum, whilst being transparent in other parts of it. IR absorbers for security printing are available, for example, from "American Dye Source", but virtually all of them have a noticeable absorption in the visible (VIS) range of the spectrum (from 400 to 700 nm).

WO2006/015414 describes IR-absorbing naphthalocyanine compounds for security printing. These compounds may have different axial substituents and a variety of central atoms.

WO 2008/006135 discloses a specific Ga naphthalocyanine compound with an ethylenoxide derived axial substituent. These types of substituents render the compounds more watersoluble.

WO 2009/012514 discloses a further specific Ga naphthalocyanine compound with a $C_{16}$alkyl axial substituent which may impart more oil solubility to the compound.

Both approaches of varying the axial substituent lead to secondary properties of the IR absorbing compounds, namely more water soluble or more soluble in organic solvents.

DESCRIPTION OF THE INVENTION

The objective of the instant invention is to provide Ga naphthalocyanine compounds with more pigmentary properties. Solubility in water or organic solvents should be very low, light stability, heat stability should be as high as possible. The advantageous absorbing properties should thereby not adversely be affected.

The problem has been solved by providing Ga naphthalocyanine compounds substituted with $C_1$-$C_6$alkoxy axial substituents, preferably $C_1$-$C_5$alkoxy axial substituents, most preferred the ethyloxy, propyloxy and butyloxy axial substituent. The compounds exhibit very high thermal and light fastness, high resistance against chemicals and solvents without losing their other advantages like colourlessness. They can be advantageously employed as IR absorbers for security printing and the laser-welding of plastics. Due to their unique application properties they are in particular suitable as IR absorbers for security printing, especially for bank notes.

In a first aspect, the invention provides naphthalocyanine compounds of formula (I)

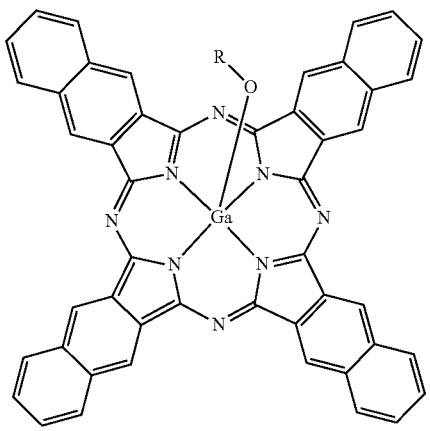

wherein R is $C_1$-$C_6$alkyl.

Preferably R is $C_1$-$C_5$alkyl.

In a specific embodiment of the invention R is ethyl, propyl or butyl.

Alkyl may be linear or branched.

Where applicable, linear $C_1$-$C_6$alkyl is preferred.

The naphthalocyanine compounds of formula (I) may be used as colourless IR absorbers, for optical filter applications, especially for plasma display panels, or for laser welding of plastics.

The afore-mentioned IR absorbers of the general formula (I) and IR absorber mixtures are especially suitable for laser welding of plastics.

The laser welding is preferably carried out using a YAG laser or using a diode laser emitting within the absorption range of the aforementioned IR absorber of the formula (I). The concentration of the IR absorber of the general formula (I) or of IR absorber mixtures is e.g. from 5 to 500 ppm, preferably from 10 to 200 ppm.

In laser welding, plastics components are welded to one another. The plastics components to be fused may have any shape. For example, at least one of the plastics components may be a film.

The compounds of the general formula (I) according to the invention are suitable for welding transparent at least translucent plastic materials. The employed plastic materials may be colourless or coloured. In principle, the plastic components to be fused may be composed of the same polymer or of different polymers. Preferably, the plastic components employed for laser welding are selected from thermoplastic polymers. However, it is also possible that neither of the plastic components to be fused is composed of thermoplastic; however, a coating of at least one part with a thermoplastic comprising at least one compound of the general formula (I) is required.

The plastic components employed for laser welding preferably comprise or consist of at least one polymer selected from polyolefins, polyolefin copolymers, polytetrafluoroethylenes, ethylene-tetrafluoroethylene copolymers, polyvinyl chlorides, polyvinylidene chlorides, polyvinyl alcohols, polyvinyl esters, polyvinyl alkanals, polyvinyl ketals, polyamides, polyimides, polycarbonates, polycarbonate blends, polyesters, polyester blends, poly(meth)acrylates, poly (meth)acrylate-styrene copolymer blends, poly(meth)acrylate-polyvinylidene difluoride blends, polyurethanes, polystyrenes, styrene copolymers, polyethers, polyether ketones and polysulfones and mixtures thereof.

Preference is given to matrix polymers from the group of the polyolefins, polyolefin copolymers, polyvinyl alkanals, polyamides, polycarbonates, polycarbonate-polyester blends, polycarbonate-styrene copolymer blends, polyesters, polyester blends, poly(meth)acrylates, poly(meth)acrylate-styrene copolymer blends, poly(meth)acrylate-polyvinylidene difluoride blends, styrene copolymers and polysulfones and mixtures thereof.

Particularly preferred polymers are transparent or at least translucent. Examples include: polypropylene, polyvinylbutyral, nylon-[6], nylon-[6,6], polycarbonate, polycarbonate-polyethylene terephthalate blends, polycarbonate-polybutylene terephthalate blends, polycarbonate-acrylonitrile/styrene/acrylonitrile copolymer blends, polycarbonate-acrylonitrile/butadiene/styrene copolymer blends, polymethyl methacrylate-acrylonitrile/butadiene/styrene copolymer blends (MABS), polyethylene terephthalate, polybutylene terephthalate, polymethyl methacrylate, impact-modified polymethyl methacrylate, polybutyl acrylate, polymethyl methacrylate-polyvinylidene difluoride blends, acrylontrile/butadiene/styrene copolymers (ABS), styrene/acrylonitrile copolymers (SAN), polyphenylenesulfone and mixtures comprising 2 or more (e.g. 2, 3, 4, 5) of the afore-mentioned polymers.

Suitable polymer preparations for laser welding comprise
A) a thermoplastic matrix polymer suitable for forming the plastics parts,
B) at least one compound of the general formula (I) as defined before,
C) optionally at least one further additive.

Those polymer preparations for laser welding are likewise in accordance with the invention and are suitable for producing fusion-bonded plastic parts with the aid of laser radiation whose wavelength is outside the visible region.

Polymer preparations for laser welding may advantageously be produced by a conventional extrusion or kneading process. The components B), and, if present, C) may be mixed from the outset, in the weight ratio corresponding to the desired end concentration, with the matrix polymer A) (direct compounding), or a distinctly higher concentration of B) and, if present, C) may initially be selected and the concentrate formed (masterbatch) subsequently diluted with further matrix polymer A) in the course of the manufacture of the parts to be fused.

Suitable additives C) are UV stabilizers, antioxidants, processing plasticizers, etc.

In addition, the polymer preparations for laser welding may comprise at least one colorant for establishing a desired hue as additive, especially transparent organic pigments and in particular dyes, for example C.I. Pigment Yellow 138, 139, 147, 183, 185 192 and 196, C.I. Pigment Orange 70, C.I. Pigment Red 149, 178 and 179, 181, 263, C.I. Pigment Violet 19 and 29, C.I. Pigment Blue 15, 15:1, 15:3 and 15:4, C.I. Pigment Green 7 and 36, C.I. Solvent Yellow 14, 21, 93, 130, 133, 145, 163, C.I. Solvent Red 52, 135, 195, 213, 214 and 225, C.I. Solvent Blue 35, 45, 67, 68, 97, 104, 122, 132, C.I. Solvent Violet 13, 46, 49, C.I. Solvent Green 3, 5 and 28, C.I. Solvent Orange 47, 60, 86, 114, and 163, C.I. Solvent Brown 35, 53, and also C.I. Disperse Yellow 54, 87, 201, C.I. Disperse Orange 30, C.I. Disperse Red 60 and C.I. Disperse Violet 57

A further possible additive group is that of additives which likewise modify the visual appearance, the mechanical properties or else the tactile properties, for example matting agents, such as titanium dioxide, chalk, barium sulfate, zinc sulfide, fillers, such as nano-particulate silicon dioxide, aluminium hydroxide, clay and other sheet silicates, glass fibers and glass spheres.

An especially suitable field of application is the use of the compounds of formula (I) in security printing.

The compounds of the general formula (I) have at least one of the following advantageous properties.
good fastness to chemicals, in particular fastness to bleaching with hypochlorite and fastness to solvents (like toluene, acetone or dichloromethane),
good fastness to boiling water,
good fastness to light,
almost colourless (i.e. minimal absorption in the VIS range of the spectrum (from 400 to 700 nm))
good heat stability,
high compatibility with a multiplicity of formulations, in particular printing ink formulations used especially in security printing.

The compounds of general formula (I) can be used inter alia for security printing, invisible and/or IR readable bar codes, the laser-welding of plastics, the curing of surface-coatings using IR radiators, the drying and curing of print, the fixing of toners on paper or plastics, optical filters for plasma display panels, laser marking of paper or plastics, the heating of plastic preforms, and for heat shielding applications.

In a further aspect, the invention provides a printing ink formulation for security printing, comprising at least one compound of the formula (I) as defined above.

In a specific embodiment the printing ink formulation, for security printing, comprises
a) at least one compound of the formula (I) as defined above,
b) a polymeric binder,
c) a solvent,
d) optionally at least one colorant, and
e) optionally at least one further additive.
More specific the printing ink formulation comprises
a) 0.0001 to 25% by weight of at least one compound of the formula (I) as defined above,
b) 5 to 74% by weight of at least one polymeric binder,
c) 1 to 94.9999% by weight of at least one solvent,
d) 0 to 25% by weight of at least one colorant, and
e) 0 to 25% by weight of at least one further additive,
wherein the sum of components a) to e) adds up to 100%.

Also an aspect of the invention is a process for the manufacture of a security document comprising the steps of printing on a substrate a printing ink formulation as described above.

In another aspect, the invention provides a security document, comprising a substrate and at least one compound of the formula (I) as defined above. The security document may be a bank note, a passport, a check, a voucher, an ID- or transaction card, a stamp and a tax label.

Yet in a further aspect, the invention provides a security document, obtainable by a printing process, wherein a printing ink formulation is employed that comprises at least one compound of the formula (I) as defined above.

The IR absorbers of formula (I) can also be used in the form of a mixture, comprising at least one compound of the general formula (I) and at least one further IR absorber different from compounds of the general formula (I). Suitable further IR absorbers are in principle all known classes of IR absorbers that are compatible with the compounds of the general formula (I). Preferred further IR absorbers are selected from polymethines, phthalocyanines, quinone-di-immonium salts, aminium salts, rylenes, inorganic IR absorbers and mixtures thereof. Further polymethine IR absorbers are preferably selected from cyanines, squaraines, croconaines and mixtures thereof. Further inorganic IR absorbers are preferably selected from indium tin oxide, antimony tin oxide, lanthanum hexaboride, tungsten bronzes, copper salts etc.

The IR absorbers can be generally used in a concentration of from 10 ppm to 25%, preferably 100 ppm to 10%, depending on the chosen application.

The afore-mentioned IR absorbers of the general formula (I) and IR absorber mixtures are especially suitable for security printing.

Security printing is the field that deals with the printing of items such as currency, passports, tamper-evident labels, stock certificates, postage stamps, identity cards, etc. The main goal of security printing is to prevent forgery, tampering or counterfeiting.

In the field of automated banknote processing, IR-absorption plays an important role. Most of the actually circulating currency carries not only visibly coloured printings, but also specific features which are only detectable in the infrared part of the spectrum. Generally, these IR-features are implemented for use by automatic currency processing equipment, in banking and vending applications (automatic teller machines, automatic vending machines, etc.), in order to recognize a determined currency bill and to verify its authenticity, in particular to discriminate it from replicas made by colour copiers.

All security documents are required to have good stability and durability. In the case of bank notes, these requirements are extreme, as bank notes are subjected to toughest use conditions by the public—they are subjected to material stress by folding, crumpling etc., subjected to abrasion, exposed to weather, exposed to bodily fluids such as perspiration, laundered, dry-cleaned, ironed etc.—and, after having been subjected to this, are expected to be as legible as when they started. Furthermore, it is essential that the documents nevertheless should have a reasonable life time, ideally of some years, despite suffering the afore-mentioned conditions. During this time, the documents, and thus the inks on them (including invisible security markings), should be resistant to fading or colour change. Hence, any ink used in a security printing process should, when cured, be robust, water-resistant, resistant to various chemicals and flexible. Moreover, as certain states are moving away from the use of paper as the substrate for bank notes, the employed printing ink formulations should be useable on plastics as well as paper.

In one aspect the present invention is directed to the use of compounds of the formula (I) for security printing, especially security printing of bank notes. The compounds of formula (I) exhibit improved resistance against chemicals and solvents as well as high light stability, particularly against UV light.

Advantageously, the compounds of the formula (I) may be used in a printing ink formulation for security printing to improve the fastness properties of the obtained print, in particular to improve the fastness to UV-light, chemicals, solvents and/or boiling water, without sacrificing the desired IR absorption properties.

In security printing, the compounds of formula (I) are added to a printing ink formulation. Suitable printing inks are water-based, oil-based or solvent-based printing inks, based on pigment or dye, for inkjet printing, flexographic printing, screen printing, intaglio printing, offset printing, laser printing or letterpress printing and for use in electrophotography. Printing inks for these printing processes usually comprise solvents, binders, and also various additives, such as plasticizers, antistatic agents or waxes. Printing inks for offset printing and letterpress printing are usually formulated as high-viscosity paste printing inks, whereas printing inks for flexographic printing and intaglio printing are usually formulated as liquid printing inks with comparatively low viscosity.

In the context of the present invention, the expression "printing ink" also encompasses formulations that in addition to at least one IR absorber of the general formula (I) comprise a colorant. The expression "printing ink" also encompasses printing lacquers that comprise no colorant.

Suitable components of printing inks are conventional and are well known to those skilled in the art. Examples of such components are described in "Printing Ink Manual", fourth edition, Leach R. H. et al. (eds.), Van Nostrand Reinhold, Wokingham, (1988). Details of printing inks and their formulation are also disclosed in "Printing Inks"-Ullmann's Encyclopedia of Industrial Chemistry, Sixth Edition, 1999 Electronic Release. A formulation of an IR-absorbing intaglio ink formulation is described in US 20080241492 A1. The disclosure of the afore-mentioned documents is incorporated herein by reference.

The printing ink formulation according to the invention contains in general from 0.0001 to 25% by weight, preferably from 0.001 to 15% by weight, in particular from 0.01 to 5% by weight, based on the total weight of the printing ink formulation, of at least one compound of formula (I), component a).

The compounds of formula (I) are present in the printing ink formulation in dissolved form or in solid form (in a finely divided state). Due to their pigment properties the solid form is preferred.

The printing ink formulation according to the invention contains in general from 5 to 74% by weight, preferably from 10 to 60% by weight, more preferably from 15 to 40% by weight, based on the total weight of the printing ink formulation, of component b).

Suitable polymeric binders b) for the printing ink formulation according to the invention are for example selected from natural resins, phenol resin, phenol-modified resins, alkyd resins, polystyrene homo- and copolymers, terpene resins, silicone resins, polyurethane resins, urea-formaldehyde resins, melamine resins, polyamide resins, polyacrylates, polymethacrylates, chlorinated rubber, vinyl ester resins, acrylic resins, epoxy resins, nitrocellulose, hydrocarbon resins, cellulose acetate, and mixtures thereof.

The printing ink formulation according to the invention can also comprise components that form a polymeric binder by a curing process. Thus, the printing ink formulation according to the invention can also be formulated to be energy-curable, e.g. able to be cured by UV light or EB (electron beam) radiation. In this embodiment, the binder comprises one or more curable monomers and/oligomers. Corresponding formulations are known in the art and can be found in standard textbooks such as the series "Chemistry & Technology of UV & EB Formulation for Coatings, Inks & Paints", published in 7 volumes in 1997-1998 by John Wiley & Sons in association with SITA Technology Limited.

Suitable monomers and oligomers (also referred to as prepolymers) include epoxy acrylates, acrylated oils, urethane acrylates, polyester acrylates, silicone acrylates, acrylated amines, and acrylic saturated resins. Further details and examples are given in "Chemistry & Technology of UV & EB Formulation for Coatings, Inks & Paints", Volume II: Prepolymers & Reactive Diluents, edited by G Webster.

If a curable polymeric binder is employed, it may contain reactive diluents, i.e. monomers which act as a solvent and which upon curing are incorporated into the polymeric binder. Reactive monomers are typically chosen from acrylates or methacrylates, and can be monofunctional or multifunctional. Examples of multifunctional monomers include polyester acrylates or methacrylates, polyol acrylates or methacrylates, and polyether acrylates or methacrylates.

In the case of printing ink formulations to be cured by UV radiation, it is usually necessary to include at least one photoinitiator to initiate the curing reaction of the monomers upon exposure to UV radiation. Examples of useful photoinitiators can be found in standard textbooks such as "Chemistry & Technology of UV & EB Formulation for Coatings, Inks & Paints", Volume III, "Photoinitiators for Free Radical Cationic and Anionic Polymerisation", 2nd edition, by J. V. Crivello & K. Dietliker, edited by G. Bradley and published in 1998 by John Wiley & Sons in association with SITA Technology Limited. It may also be advantageous to include a sensitizer in conjunction with the photoinitiator in order to achieve efficient curing.

The printing ink formulation according to the invention contains in general from 1 to 94.9999% by weight, preferably from 5 to 90% by weight, in particular from 10 to 85% by weight, based on the total weight of the printing ink formulation, of a solvent c).

Suitable solvents are selected from water, organic solvents and mixtures thereof. For the purpose of the invention, reactive monomers which also act as solvents are regarded as part of the afore-mentioned binder component b).

Examples of solvents comprise water; alcohols, e.g. ethanol, 1-propanol, 2-propanol, ethylene glycol, propylene glycol, diethylene glycol and ethoxy propanol; esters, e.g. ethyl acetate, isopropyl acetate, n-propyl acetate and n-butyl acetate; hydrocarbons, e.g. toluene, xylene, mineral oils and vegetable oils, and mixtures thereof.

The printing ink formulation according to the invention may contain an additional colorant d). Preferably, the printing ink formulation contains from 0 to 25% by weight, more preferably from 0.1 to 20% by weight, in particular from 1 to 15% by weight, based on the total weight of the printing ink formulation, of a colorant d).

Suitable colorants d) are selected conventional dyes and in particular conventional pigments. The term "pigment" is used in the context of this invention comprehensively to identify all pigments and fillers, examples being colour pigments, white pigments, and inorganic fillers. These include inorganic white pigments, such as titanium dioxide, preferably in the rutile form, barium sulfate, zinc oxide, zinc sulfide, basic lead carbonate, antimony trioxide, lithopones (zinc sulfide+barium sulfate), or coloured pigments, examples being iron oxides, carbon black, graphite, zinc yellow, zinc green, ultramarine, manganese black, antimony black, manganese violet, Paris blue or Schweinfurt green. Besides the inorganic pigments the printing ink formulation of the invention may also comprise organic colour pigments, examples being sepia, gamboge, Cassel brown, toluidine red, para red, Hansa yellow, indigo, azo dyes, anthraquinonoid and indigoid dyes, and also dioxazine, quinacridone, phthalocyanine, isoindolinone, and metal complex pigments. Also suitable are synthetic white pigments with air inclusions to increase the light scattering, such as the Rhopaque® dispersions. Suitable fillers are, for example, aluminosilicates, such as feldspars, silicates, such as kaolin, talc, mica, magnesite, alkaline earth metal carbonates, such as calcium carbonate, in the form for example of calcite or chalk, magnesium carbonate, dolomite, alkaline earth metal sulfates, such as calcium sulfate, silicon dioxide, etc.

The printing ink formulation according to the invention may contain at least one additive e). Preferably, the printing ink formulation contains from 0 to 25% by weight, more preferably from 0.1 to 20% by weight, in particular from 1 to 15% by weight, based on the total weight of the printing ink formulation, of at least one component e).

Suitable additives (component e)) are selected from plasticizers, waxes, siccatives, antitatic agents, chelators, antioxidants, stabilizers, adhesion promoters, surfactants, flow control agents, defoamers, biocides, thickeners, etc. and combinations thereof. These additives serve in particular for fine adjustment of the application-related properties of the printing ink, examples being adhesion, abrasion resistance, drying rate, or slip.

The printing ink formulations according to the invention are advantageously prepared in a conventional manner, for example by mixing the individual components. As mentioned earlier, the compound of formula (I) is present in the printing ink formulations in a dissolved or finely divided solid form. Additional colorants may be employed in the printing ink formulation of the invention or in a separate ink formulation. When additional colorants are to be employed in a separate formulation, the time of application of the printing ink formulation according to the invention is usually immaterial. The printing ink formulation according to the invention can for example be applied first and then be overprinted with conventional printing inks. But it is also possible to reverse this sequence or, alternatively, to apply the printing ink formulation according to the invention in a mixture with conventional printing inks. In every case the prints are readable with suitable light sources.

Primers can be applied prior to the printing ink formulation according to the invention. By way of example, the primers are applied in order to improve adhesion to the substrate. It is also possible to apply additional printing lacquers, e.g. in the form of a covering to protect the printed image. Additional printing lacquers may also be applied to serve aesthetic purposes, or serve to control application-related properties. By way of example, suitably formulated additional printing lacquers can be used to influence the roughness of the surface of the substrate, the electrical properties, or the water-vapour-condensation properties. Printing lacquers are usually applied in-line by means of a lacquering system on the printing machine employed for printing the printing ink formulation according to the invention.

The printing ink formulations according to the invention are also suitable for use in multilayer materials. Multilayer materials are e.g. composed of two or more plastics foils, such as polyolefin foils, metal foils, or metallised plastics foils, which are bonded to one another, by way of example, via lamination or with the aid of suitable laminating adhesives. These composites may also comprise other functional layers, such as odour-barrier layers or water-vapour barriers.

The printing ink formulations may additionally comprise one or more UV absorbers. UV absorbers are well known in the plastics, coatings and cosmetic industry. Examples for suitable UV absorbers are subsequently given.

2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonyl-ethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

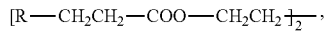

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethyl butyl)-5'-(α,α-dimethylbenzyl)-phenyl]benzotriazole.

2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

Acrylates, for example ethyl α-cyano-β,β-diphenylacrylate, isooctyl α-cyano-β,β-diphenylacrylate, methyl α-carbomethoxycinnamate, methyl α-cyano-β-methyl-β-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, neopentyl tetra(α-cyano-β,β-diphenylacrylate.

Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

Various features and aspects of the present invention are illustrated further in the examples that follow. While these examples are presented to show one skilled in the art how to operate within the scope of this invention, they are not to serve as a limitation on the scope of the invention where such scope is only defined in the claims. Unless otherwise indicated in the following examples and elsewhere in the specification and claims, all parts and percentages are by weight, temperatures are in degrees centigrade and pressures are at or near atmospheric.

EXAMPLES

Preparation Examples

Pentoxy-Ga-Naphthalocyanine:
A solution of sodium pentoxide made of 6.2 g sodium in 155 g 1-pentanol is prepared and slowly added to a solution of 15.0 g gallium chloride in 210 g toluene at room temperature. To the resulting suspension is added a mixture of 61.3 g naphthalene-2,3-dicarbonitrile, 240 g triethylenglycol-dimethylether and 240 g toluene. Toluene and the excess of 1-pentanol are distilled off under reduced pressure at 100° C. and the reaction mixture is stirred at 170° C. for 5 hours. The suspension is first cooled to 80° C., 250 g DMF is added, and then further cooled to room temperature. The green solid is collected by filtration, successively washed with DMF, acetone and water and then dried. Yield: 34.2 g (47.1%)

Butoxy-Ga-Naphthalocyanine:
A solution of sodium butoxide made of 6.2 g sodium in 155 g 1-butanol is prepared and slowly added to a solution of 15.0 g gallium chloride in 210 g toluene at room temperature. To the resulting suspension is added a mixture of 61.3 g naphthalene-2,3-dicarbonitrile, 240 g triethylenglycol-dimethylether and 240 g toluene. Toluene and the excess of 1-butanol are distilled off under reduced pressure at 100°

C. and the reaction mixture is stirred at 170° C. for 7 hours. The suspension is first cooled to 80° C., 250 g DMF is added, and then further cooled to room temperature. The green solid is collected by filtration, successively washed with DMF, acetone and water and then dried. Yield: 46.6 g (65.3%)

Propoxy-Ga-Naphthalocyanine:

A solution of sodium propoxide made of 10.4 g sodium in 260 g 1-propanol is prepared and slowly added to a solution of 25.0 g gallium chloride in 280 g toluene at room temperature. To the resulting suspension is added a mixture of 102.4 g naphthalene-2,3-dicarbonitrile, 300 g triethylenglycol-dimethylether and 300 g toluene. Toluene and the excess of 1-propanol are distilled off under reduced pressure at 100° C. and the reaction mixture is and then further cooled to room temperature. The green solid is collected by filtration, successively washed with DMF, acetone and water and then dried. Yield: 49.8 g (42.5%)

Ethoxy-Ga-Naphthalocyanine:

A solution of sodium ethoxide made of 10.4 g sodium in 260 g ethanol is prepared and slowly added to a solution of 25.0 g gallium chloride in 280 g toluene at room temperature. To the resulting suspension is added a mixture of 102.4 g naphthalene-2,3-dicarbonitrile, 300 g triethylenglycol-dimethylether and 300 g toluene. Toluene and the excess of ethanol are distilled off by heating to 100° C. under slightly reduced pressure and the reaction mixture is stirred at 170° C. for 6 hours. The suspension is first cooled to 80° C., 360 g DMF is added, and then further cooled to room temperature. The green solid is collected by filtration, successively washed with DMF, acetone and water and then dried. Yield: 43.4 g (36.9%)

Methoxy-Ga-Naphthalocyanine:

A solution of sodium methoxide made of 10.4 g sodium in 260 g methanol is prepared and slowly added to a solution of 25.0 g gallium chloride in 280 g toluene at room temperature. To the resulting suspension is added a mixture of 102.4 g naphthalene-2,3-dicarbonitrile, 300 g triethylenglycol-dimethylether and 300 g toluene. Toluene and the excess of methanol are distilled off by heating to 100° C. under slightly reduced pressure and the reaction mixture is stirred at 170° C. for 6 hours. The suspension is first cooled to 80° C., 360 g DMF is added, and then further cooled to room temperature. The green solid is collected by filtration, successively washed with DMF, acetone and water and then dried. Yield: 44.6 g (38.6%)

Pigment finishing methods can be optionally applied to the materials described in the examples above, e.g. kneading or milling.

Application Example

An offset ink is prepared by mixing the following components by means of an automatic pigment muller:

| | |
|---|---|
| Offset varnish | 1000 mg |
| IR absorber, prepared as described above (crude or after pigment finishing) | 40 mg |
| Siccative | 20 mg |

Immediately afterwards the freshly prepared offset ink is printed onto cotton paper with a printability tester (IGT Orange Proofer). Ink transfer: 1 gram/square centimeter. Remission curves are measured afterwards with an UV/VIS/IR spectrophotometer. The remission values are given in the following Table 1.

TABLE 1

| Wavelength | % R Propoxy-Ga-Naphthalocyanine crude | % R Butoxy-Ga-Naphthalocyanine crude | % R Propoxy-Ga-Naphthalocyanine kneaded | % R Butoxy-Ga-Naphthalocyanine kneaded |
|---|---|---|---|---|
| 1600 | 90.0 | 91.0 | 88.2 | 88.9 |
| 1590 | 90.3 | 91.2 | 88.7 | 89.3 |
| 1580 | 90.5 | 91.4 | 88.7 | 89.4 |
| 1570 | 90.6 | 91.5 | 88.8 | 89.4 |
| 1560 | 90.7 | 91.7 | 89.0 | 89.7 |
| 1550 | 90.9 | 91.8 | 89.4 | 89.9 |
| 1540 | 90.8 | 91.7 | 89.3 | 89.8 |
| 1530 | 90.7 | 91.8 | 89.1 | 89.8 |
| 1520 | 90.7 | 91.7 | 89.1 | 89.6 |
| 1510 | 90.6 | 91.7 | 89.3 | 89.8 |
| 1500 | 90.9 | 91.7 | 89.3 | 89.9 |
| 1490 | 91.1 | 91.8 | 89.4 | 89.9 |
| 1480 | 91.1 | 92.0 | 89.6 | 90.0 |
| 1470 | 90.8 | 91.7 | 89.3 | 89.7 |
| 1460 | 90.4 | 91.3 | 88.7 | 89.2 |
| 1450 | 90.1 | 91.1 | 88.4 | 88.9 |
| 1440 | 89.6 | 90.7 | 88.0 | 88.6 |
| 1430 | 89.0 | 90.1 | 87.6 | 88.1 |
| 1420 | 88.4 | 89.6 | 86.8 | 87.4 |
| 1410 | 88.0 | 89.1 | 86.4 | 87.0 |
| 1400 | 87.6 | 88.8 | 85.9 | 86.7 |
| 1390 | 87.5 | 88.6 | 85.9 | 86.6 |
| 1380 | 87.7 | 88.8 | 86.1 | 86.8 |
| 1370 | 87.8 | 89.0 | 86.3 | 86.9 |
| 1360 | 87.9 | 89.1 | 86.4 | 86.9 |
| 1350 | 87.9 | 89.2 | 86.3 | 87.0 |
| 1340 | 87.9 | 89.3 | 86.5 | 87.2 |
| 1330 | 88.0 | 89.4 | 86.7 | 87.2 |
| 1320 | 88.0 | 89.5 | 86.8 | 87.3 |
| 1310 | 88.0 | 89.4 | 86.9 | 87.4 |
| 1300 | 88.1 | 89.4 | 87.0 | 87.4 |
| 1290 | 88.1 | 89.4 | 86.9 | 87.4 |
| 1280 | 88.2 | 89.5 | 86.9 | 87.5 |

TABLE 1-continued

| Wavelength | % R Propoxy-Ga-Naphthalocyanine crude | % R Butoxy-Ga-Naphthalocyanine crude | % R Propoxy-Ga-Naphthalocyanine kneaded | % R Butoxy-Ga-Naphthalocyanine kneaded |
|---|---|---|---|---|
| 1270 | 88.3 | 89.5 | 87.0 | 87.6 |
| 1260 | 88.2 | 89.5 | 87.1 | 87.5 |
| 1250 | 88.3 | 89.5 | 87.1 | 87.5 |
| 1240 | 88.3 | 89.5 | 87.0 | 87.6 |
| 1230 | 88.1 | 89.4 | 86.9 | 87.5 |
| 1220 | 88.1 | 89.2 | 86.9 | 87.3 |
| 1210 | 88.0 | 89.2 | 86.7 | 87.2 |
| 1200 | 87.8 | 89.0 | 86.8 | 87.2 |
| 1190 | 87.8 | 88.9 | 86.6 | 87.0 |
| 1180 | 87.8 | 88.9 | 86.7 | 87.1 |
| 1170 | 87.9 | 89.1 | 86.6 | 87.2 |
| 1160 | 88.1 | 89.3 | 86.8 | 87.4 |
| 1150 | 88.1 | 89.4 | 86.9 | 87.4 |
| 1140 | 88.1 | 89.5 | 87.0 | 87.5 |
| 1130 | 88.1 | 89.4 | 87.1 | 87.5 |
| 1120 | 88.2 | 89.5 | 87.3 | 87.7 |
| 1110 | 88.1 | 89.7 | 87.2 | 87.8 |
| 1100 | 87.8 | 89.7 | 87.3 | 87.9 |
| 1090 | 87.5 | 89.6 | 87.3 | 87.7 |
| 1080 | 86.9 | 89.5 | 87.3 | 87.6 |
| 1070 | 86.2 | 89.2 | 87.0 | 87.4 |
| 1060 | 85.2 | 88.9 | 86.7 | 87.0 |
| 1050 | 84.2 | 88.5 | 86.3 | 86.6 |
| 1040 | 83.3 | 88.1 | 86.1 | 86.1 |
| 1030 | 82.3 | 87.6 | 85.6 | 85.6 |
| 1020 | 81.4 | 86.9 | 84.8 | 84.6 |
| 1010 | 80.4 | 86.0 | 84.0 | 83.4 |
| 1000 | 79.4 | 85.0 | 82.8 | 82.0 |
| 990 | 78.4 | 83.9 | 81.6 | 80.3 |
| 980 | 77.2 | 82.4 | 79.9 | 78.3 |
| 970 | 75.6 | 80.7 | 78.0 | 75.9 |
| 960 | 73.5 | 78.8 | 75.4 | 73.2 |
| 950 | 71.1 | 76.7 | 72.5 | 70.2 |
| 940 | 68.3 | 74.5 | 68.8 | 66.9 |
| 930 | 65.3 | 72.6 | 64.8 | 63.5 |
| 920 | 62.2 | 70.8 | 60.6 | 60.2 |
| 910 | 59.4 | 69.3 | 56.5 | 57.2 |
| 900 | 57.2 | 68.2 | 52.9 | 54.8 |
| 890 | 55.5 | 67.5 | 50.2 | 52.7 |
| 880 | 54.7 | 66.9 | 47.9 | 51.0 |
| 870 | 54.2 | 66.6 | 46.2 | 49.3 |
| 860 | 54.0 | 66.1 | 44.0 | 47.4 |
| 850 | 53.1 | 65.1 | 41.7 | 45.6 |
| 840 | 50.2 | 61.7 | 35.7 | 39.7 |
| 830 | 50.1 | 61.4 | 35.0 | 38.7 |
| 820 | 50.1 | 60.6 | 34.6 | 38.0 |
| 810 | 50.2 | 60.3 | 34.5 | 37.6 |
| 800 | 50.5 | 60.5 | 34.6 | 37.3 |
| 790 | 50.5 | 60.8 | 34.2 | 36.6 |
| 780 | 50.6 | 60.9 | 33.4 | 35.7 |
| 770 | 50.4 | 60.7 | 32.0 | 34.2 |
| 760 | 50.3 | 60.4 | 30.3 | 32.5 |
| 750 | 50.6 | 60.4 | 28.9 | 31.0 |
| 740 | 51.4 | 60.9 | 28.4 | 30.4 |
| 730 | 52.9 | 62.1 | 29.3 | 31.1 |
| 720 | 55.0 | 63.8 | 31.7 | 33.0 |
| 710 | 57.2 | 65.8 | 35.1 | 36.0 |
| 700 | 59.5 | 67.8 | 39.1 | 39.7 |
| 690 | 62.0 | 69.9 | 43.5 | 43.8 |
| 680 | 64.6 | 72.2 | 48.2 | 48.4 |
| 670 | 67.7 | 74.5 | 53.5 | 53.7 |
| 660 | 70.6 | 76.8 | 58.7 | 58.7 |
| 650 | 73.3 | 79.0 | 63.8 | 63.8 |
| 640 | 75.8 | 80.9 | 68.5 | 68.4 |
| 630 | 78.0 | 82.6 | 72.5 | 72.4 |
| 620 | 79.9 | 84.0 | 75.9 | 75.8 |
| 610 | 81.8 | 85.3 | 78.6 | 78.5 |
| 600 | 83.3 | 86.2 | 80.6 | 80.5 |
| 590 | 84.6 | 87.0 | 82.1 | 81.8 |
| 580 | 85.6 | 87.6 | 83.0 | 82.8 |
| 570 | 86.3 | 88.2 | 83.7 | 83.6 |
| 560 | 86.6 | 88.4 | 83.9 | 83.8 |
| 550 | 86.3 | 88.2 | 83.3 | 83.1 |
| 540 | 85.2 | 87.5 | 82.0 | 81.9 |
| 530 | 83.9 | 86.7 | 80.8 | 81.1 |
| 520 | 83.4 | 86.4 | 80.5 | 81.0 |

TABLE 1-continued

| Wavelength | % R Propoxy-Ga-Naphthalocyanine crude | % R Butoxy-Ga-Naphthalocyanine crude | % R Propoxy-Ga-Naphthalocyanine kneaded | % R Butoxy-Ga-Naphthalocyanine kneaded |
|---|---|---|---|---|
| 510 | 82.9 | 86.0 | 79.8 | 80.2 |
| 500 | 81.5 | 85.0 | 77.5 | 77.6 |
| 490 | 78.2 | 82.7 | 72.3 | 72.6 |
| 480 | 72.6 | 79.2 | 65.1 | 65.8 |
| 470 | 67.5 | 76.2 | 58.6 | 60.0 |
| 460 | 66.4 | 75.2 | 56.2 | 57.8 |
| 450 | 67.2 | 75.7 | 56.2 | 57.3 |
| 440 | 66.9 | 76.1 | 54.9 | 56.1 |
| 430 | 67.0 | 76.7 | 54.1 | 55.6 |
| 420 | 67.9 | 78.1 | 54.1 | 55.7 |
| 410 | 68.7 | 79.5 | 53.5 | 55.4 |
| 400 | 69.7 | 81.0 | 52.4 | 54.5 |

The invention claimed is:

1. A printing ink formulation, comprising:
at least one compound of the formula (I)

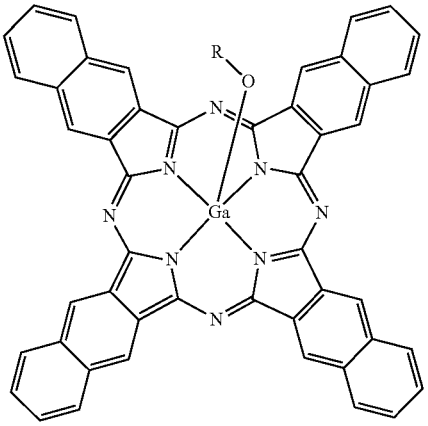

wherein R is $C_1$-$C_6$alkyl.

2. The printing ink formulation according to claim 1, comprising
a) 0.0001 to 25% by weight of at least one compound of the formula (I),
b) 5 to 74% by weight of at least one polymeric binder,
c) 1 to 94.9999% by weight of at least one solvent,
d) 0 to 25% by weight of at least one colorant, and
e) 0 to 25% by weight of at least one further additive,
wherein the sum of components a) to e) adds up to 100%.

3. A process for the manufacture of a security document, the process comprising:
printing on a substrate the printing ink formulation according to claim 1.

4. A security document, comprising:
a substrate; and obtainable by printing the printing ink formulation according to claim 1 on the substrate.

5. The security document according to claim 4, which is in the form of a bank note, a passport, a check, a voucher, an ID- or transaction card, a stamp, or a tax label.

6. A method for filtering IR radiation, the method comprising:
irradiating the printing ink formulation according to claim 1,
wherein said printing ink formulation is present in an optical filter, a plasma display panel, or a polymer.

7. A method of detecting an IR-absorbing composition, the method comprising:
printing on a substrate the printing ink formulation according to claim 1, and irradiating the substrate having present thereon an IR-absorbing.

8. A method of bonding a printing ink formulation to a substrate, the method comprising:
depositing the printing ink formulation according to claim 1 onto a substrate.

9. The printing ink formulation according to claim 1, wherein R is $C_1$-$C_5$alkyl.

10. The printing ink formulation according to claim 1, wherein R is ethyl, propyl or butyl.

11. The security document according to claim 4, wherein R is $C_1$-$C_5$alkyl.

12. The security document according to claim 4, wherein R is ethyl, propyl or butyl.

13. The method for filtering IR radiation according to claim 6, wherein R is $C_1$-$C_5$alkyl.

14. The method for filtering IR radiation according to claim 6, wherein R is ethyl, propyl or butyl.

15. The method of detecting an IR-absorbing composition according to claim 7, wherein R is $C_1$-$C_5$alkyl.

16. The method of detecting an IR-absorbing composition according to claim 7, wherein R is ethyl, propyl or butyl.

17. The method of bonding a printing ink formulation to a substrate according to claim 8, wherein R is $C_1$-$C_5$alkyl.

18. The method of bonding a printing ink formulation to a substrate according to claim 8, wherein R is ethyl, propyl or butyl.

19. The printing ink formulation according to claim 1, further comprising:
a polymeric binder,
a solvent,
optionally at least one colorant, and
optionally at least one further additive.

* * * * *

UNITED STATES PATENT AND TRADEMARK OFFICE
CERTIFICATE OF CORRECTION

| | | Page 1 of 2 |
|---|---|---|
| PATENT NO. | : 10,557,047 B2 | |
| APPLICATION NO. | : 15/307964 | |
| DATED | : February 11, 2020 | |
| INVENTOR(S) | : Hans Reichert et al. | |

It is certified that error appears in the above-identified patent and that said Letters Patent is hereby corrected as shown below:

On the Title Page

In Column 2, item (56), Foreign Patent Documents, Line 6, delete "7/2008" and insert -- 1/2008 --.

In the Specification

In Column 3, Line 38, delete "acrylontrile" and insert -- acrylonitrile --.

In Column 4, Line 11, delete "57" and insert -- 57. --;

In Column 4, Line 22, delete "properties." and insert -- properties: --.

In Column 8, Line 23, delete "e))" and insert -- e) --;

In Column 8, Line 24, delete "antitatic" and insert -- antistatic --.

In Column 9, Line 39, delete "benzotriazol" and insert -- benzotriazole --;

In Column 9, Line 42, delete "tetramethyl butyl" and insert -- tetramethylbutyl --;

In Column 9, Line 58, delete "β" and insert -- p --;

In Column 9, Line 62, delete "(α" and insert -- α --;

In Column 9, Line 67, delete "ethoxanilide" and insert -- ethoxyanilide --.

In Column 10, Lines 51-52, delete "triethylenglycol" and insert -- triethyleneglycol --.

In Column 11, Line 15, delete "is and" and insert -- is stirred at 170°C for 6 hours. The suspension is first cooled to 80°C, 360g DMF is added, and --.

Signed and Sealed this
Seventh Day of July, 2020

Andrei Iancu
*Director of the United States Patent and Trademark Office*

In the Claims

In Column 15, Line 43, Claim 2, delete "comprising" and insert -- comprising: --.